(12) United States Patent
Kong et al.

(10) Patent No.: US 7,662,552 B2
(45) Date of Patent: Feb. 16, 2010

(54) METHOD OF DIAGNOSING AND TREATING LESION OF CRYSTALLINE LENS USING HUMAN CRYGS GENE AND CODING PRODUCT THEREOF

(75) Inventors: Xiangyin Kong, Shanghai (CN); Lei Bu, Shanghai (CN); Guoping Zhao, Shanghai (CN); Shunsheng Yan, Shanghai (CN); Meilei Jin, Shanghai (CN); Yerjiang Sulitang, Shanghai (CN); Yiping Jin, Shanghai (CN); Liandian Hu, Shanghai (CN)

(73) Assignee: Shanghai Institutes of Biological Science, Chinese Academy of Sciences, Shanghai (CN)

( * ) Notice: Subject to any disclaimer, the term of this patent is extended or adjusted under 35 U.S.C. 154(b) by 22 days.

(21) Appl. No.: 10/362,817

(22) PCT Filed: Aug. 24, 2001

(86) PCT No.: PCT/CN01/01274

§ 371 (c)(1),
(2), (4) Date: Feb. 25, 2003

(87) PCT Pub. No.: WO02/40667

PCT Pub. Date: May 23, 2002

(65) Prior Publication Data

US 2003/0186294 A1    Oct. 2, 2003

(30) Foreign Application Priority Data

Aug. 25, 2000   (CN)   ............................... 00 1 19756

(51) Int. Cl.
*C12Q 1/68* (2006.01)
*C12P 19/34* (2006.01)
*C07H 21/02* (2006.01)

(52) U.S. Cl. .......... 435/6; 435/91.2; 536/23.1
(58) Field of Classification Search ............. None
See application file for complete search history.

(56) References Cited

FOREIGN PATENT DOCUMENTS

WO   WO 9830677 A1   7/1998

OTHER PUBLICATIONS

Sinha D, Esumi N, Jaworski C, Kozak CA, Pierce E, Wistow G.., Cloning and mapping the mouse Crygs gene and non-lens expression of [gamma]S-crystallin.Mol Vis. Apr. 30, 1998;4: p. 8.*
Mummidi (2000) Journal of Bilogical Chemistry, vol. 275, No. 25, pp. 18946-18961.*
Bork (1993) Protein Science vol. 2, pp. 31-40.*
Juppner (1995) Bone, vol. 17, No. 2, pp. 39S-42S.*
Sun H, Ma Z, Li Y, Liu B, Li Z, Ding X, Gao Y, Ma W, Tang X, Li X, Shen Y. Gamma-S crystallin gene (CRYGS) mutation causes dominant progressive cortical cataract in humans.J Med Genet. Sep. 2005;42(9):706-10.*
dbSNP for rs4165301, available online from www.ncbi.nlm.nih.gov/SNP. pp. 1-4.*
GeneCard output for CRYGS, available from www.genecards.org, pp. 1-11.*
Hegele RA 'SNP judgments and freedom of association.'Arterioscler Thromb Vasc Biol. Jul. 1, 2002;22(7):1058-61.*

* cited by examiner

*Primary Examiner*—Stephen Kapushoc
(74) *Attorney, Agent, or Firm*—Merchant & Gould P.C.

(57) ABSTRACT

The method of diagnosing lesions of crystalline lens such as cataract is disclosed. It comprises detecting variation of crygs gene, transcript and/or protein of individuals compared with normalty. The individual suffers from cataract more possible than normalty when occurring the variation. The present invention also discloses the method and pharmaceutical composition of treating lesions of crystalline lens such as cataract.

3 Claims, 3 Drawing Sheets

Cataract model mice

SEQ ID NO: 36

Normal F2 mice

SEQ ID NO: 37

Wild type mice

SEQ ID NO: 38

SEQUENCE LISTING

```
<160> NUMBER OF SEQ ID NOS: 45

<210> SEQ ID NO 1
<211> LENGTH: 17
<212> TYPE: DNA
<213> ORGANISM: Artificial
<220> FEATURE:
<223> OTHER INFORMATION: Synthetic Eco RI Adapter

<400> SEQUENCE: 1
ctcgtagact gcgtacc                                                          17

<210> SEQ ID NO 2
<211> LENGTH: 18
<212> TYPE: DNA
<213> ORGANISM: Artificial
<220> FEATURE:
<223> OTHER INFORMATION: Synthetic Eco RI Adapter

<400> SEQUENCE: 2
ttaaccatgc gtcagatg                                                         18

<210> SEQ ID NO 3
<211> LENGTH: 16
<212> TYPE: DNA
<213> ORGANISM: Artificial
<220> FEATURE:
<223> OTHER INFORMATION: Synthetic Mse I Adapter

<400> SEQUENCE: 3
gacgatgagt cctgag                                                           16

<210> SEQ ID NO 4
<211> LENGTH: 14
<212> TYPE: DNA
<213> ORGANISM: Artificial
<220> FEATURE:
<223> OTHER INFORMATION: Synthetic Mse I Adapter

<400> SEQUENCE: 4
atgagtcctg agta                                                             14

<210> SEQ ID NO 5
<211> LENGTH: 16
<212> TYPE: DNA
<213> ORGANISM: Artificial
<220> FEATURE:
<223> OTHER INFORMATION: Synthetic Taq I Adapter

<400> SEQUENCE: 5
```

-continued gacgatgagt cctgag                                           16

<210> SEQ ID NO 6
<211> LENGTH: 14
<212> TYPE: DNA
<213> ORGANISM: Artificial
<220> FEATURE:
<223> OTHER INFORMATION: Synthetic Taq I Adapter

<400> SEQUENCE: 6
gcgagtcctg agta                                             14

<210> SEQ ID NO 7
<211> LENGTH: 17
<212> TYPE: DNA
<213> ORGANISM: Artificial
<220> FEATURE:
<223> OTHER INFORMATION: Eco RI pre-amplification Primer

<400> SEQUENCE: 7
gactgcgtac caattcc                                          17

<210> SEQ ID NO 8
<211> LENGTH: 17
<212> TYPE: DNA
<213> ORGANISM: Artificial
<220> FEATURE:
<223> OTHER INFORMATION: Mse I pre-amplification Primer

<400> SEQUENCE: 8
gatgagtcct gagtaac                                          17

<210> SEQ ID NO 9
<211> LENGTH: 17
<212> TYPE: DNA
<213> ORGANISM: Artificial
<220> FEATURE:
<223> OTHER INFORMATION: Taq I pre-amplification Primer

<400> SEQUENCE: 9
gatgagtcct gagcgaa                                          17

<210> SEQ ID NO 10
<211> LENGTH: 35
<212> TYPE: DNA
<213> ORGANISM: Artificial
<220> FEATURE:
<223> OTHER INFORMATION: Eco RI selective amplification Primer
<220> FEATURE:
<221> NAME/KEY: misc_feature
<222> LOCATION: (35)..(35)
<223> OTHER INFORMATION: n is a, c, g, or t

<400> SEQUENCE: 10
cacgacgttg taaaacgact gcgtaccaat tccan                      35

<210> SEQ ID NO 11
<211> LENGTH: 19
<212> TYPE: DNA
<213> ORGANISM: Artificial
<220> FEATURE:
<223> OTHER INFORMATION: Mse I selective amplification Primer
<220> FEATURE:
<221> NAME/KEY: misc_feature
<222> LOCATION: (18)..(19)
<223> OTHER INFORMATION: n is a, c, g, or t

<400> SEQUENCE: 11

```
gatgagtcct gagtaacnn                                                    19

<210> SEQ ID NO 12
<211> LENGTH: 19
<212> TYPE: DNA
<213> ORGANISM: Artificial
<220> FEATURE:
<223> OTHER INFORMATION: Tzq I selective amplification Primer
<220> FEATURE:
<221> NAME/KEY: misc_feature
<222> LOCATION: (18)..(19)
<223> OTHER INFORMATION: n is a, c, g, or t

<400> SEQUENCE: 12
gatgagtcct gagcgaann                                                    19

<210> SEQ ID NO 13
<211> LENGTH: 20
<212> TYPE: DNA
<213> ORGANISM: Artificial
<220> FEATURE:
<223> OTHER INFORMATION: Forward Primer

<400> SEQUENCE: 13
cattttcatg tctaagccag                                                   20

<210> SEQ ID NO 14
<211> LENGTH: 20
<212> TYPE: DNA
<213> ORGANISM: Artificial
<220> FEATURE:
<223> OTHER INFORMATION: Reverse Primer

<400> SEQUENCE: 14
agagtgaaat ggatcagatg                                                   20

<210> SEQ ID NO 15
<211> LENGTH: 20
<212> TYPE: DNA
<213> ORGANISM: Artificial
<220> FEATURE:
<223> OTHER INFORMATION: Crygs-1 Forward Primer

<400> SEQUENCE: 15
tagggctggg cgagcattac                                                   20

<210> SEQ ID NO 16
<211> LENGTH: 20
<212> TYPE: DNA
<213> ORGANISM: Artificial
<220> FEATURE:
<223> OTHER INFORMATION: Crygs-1 Reverse Primer

<400> SEQUENCE: 16
caaaggttga ttcccgcact                                                   20

<210> SEQ ID NO 17
<211> LENGTH: 20
<212> TYPE: DNA
<213> ORGANISM: Artificial
<220> FEATURE:
<223> OTHER INFORMATION: Crygs-2 Forward Primer

<400> SEQUENCE: 17
gtccctctgc ctgtagtcct                                                   20
```

<210> SEQ ID NO 18
<211> LENGTH: 21
<212> TYPE: DNA
<213> ORGANISM: Artificial
<220> FEATURE:
<223> OTHER INFORMATION: Crygs-2 Reverse Primer

<400> SEQUENCE: 18
acaagccttt tccatcttct c                                          21

<210> SEQ ID NO 19
<211> LENGTH: 20
<212> TYPE: DNA
<213> ORGANISM: Artificial
<220> FEATURE:
<223> OTHER INFORMATION: Crygs-3 Forward Primer

<400> SEQUENCE: 19
ccagctcctc agctcactca                                            20

<210> SEQ ID NO 20
<211> LENGTH: 20
<212> TYPE: DNA
<213> ORGANISM: Artificial
<220> FEATURE:
<223> OTHER INFORMATION: Crygs-3 Reverse Primer

<400> SEQUENCE: 20
ccatccaacg ctggtattca                                            20

<210> SEQ ID NO 21
<211> LENGTH: 20
<212> TYPE: DNA
<213> ORGANISM: Artificial
<220> FEATURE:
<223> OTHER INFORMATION: Crygs-4 Forward Primer

<400> SEQUENCE: 21
ccgctcgtac ctaagtcgct                                            20

<210> SEQ ID NO 22
<211> LENGTH: 20
<212> TYPE: DNA
<213> ORGANISM: Artificial
<220> FEATURE:
<223> OTHER INFORMATION: Crygs-4 Reverse Primer

<400> SEQUENCE: 22
aggaaagatg cggggtcgtg                                            20

<210> SEQ ID NO 23
<211> LENGTH: 20
<212> TYPE: DNA
<213> ORGANISM: Artificial
<220> FEATURE:
<223> OTHER INFORMATION: Crygs-5 Forward Primer

<400> SEQUENCE: 23
ccgagttcct gacatgctaa                                            20

<210> SEQ ID NO 24
<211> LENGTH: 21
<212> TYPE: DNA
<213> ORGANISM: Artificial
<220> FEATURE:
<223> OTHER INFORMATION: Crygs-5 Reverse Primer

```
<400> SEQUENCE: 24
atactgtctg ccacggtagt t                                              21

<210> SEQ ID NO 25
<211> LENGTH: 24
<212> TYPE: DNA
<213> ORGANISM: Artificial
<220> FEATURE:
<223> OTHER INFORMATION: Crygs-6 Forward Primer

<400> SEQUENCE: 25
gagattcatt cctgtaaggt ggta                                           24

<210> SEQ ID NO 26
<211> LENGTH: 22
<212> TYPE: DNA
<213> ORGANISM: Artificial
<220> FEATURE:
<223> OTHER INFORMATION: Crygs-6 Reverse Primer

<400> SEQUENCE: 26
cctcagggag aactctatgg tc                                             22

<210> SEQ ID NO 27
<211> LENGTH: 21
<212> TYPE: DNA
<213> ORGANISM: Artificial
<220> FEATURE:
<223> OTHER INFORMATION: Crygs-7 Forward Primer

<400> SEQUENCE: 27
tctggataag aaggagtacc g                                              21

<210> SEQ ID NO 28
<211> LENGTH: 22
<212> TYPE: DNA
<213> ORGANISM: Artificial
<220> FEATURE:
<223> OTHER INFORMATION: Crygs-7 Reverse Primer

<400> SEQUENCE: 28
ggtcctaaaa gcaattaaga ag                                             22

<210> SEQ ID NO 29
<211> LENGTH: 702
<212> TYPE: DNA
<213> ORGANISM: Mus musculus

<400> SEQUENCE: 29
agctgccctg gatctctctc agtagtgcgg gaatcaacct ttgcacatac aatgtctaaa     60
actggaggca agattagttt ctacgaagac cgaaattttc aaggccgccg ctatgactgc    120
gactgcgact gcgcagactt ccgctcgtac ctaagtcgct gcaactccat tagagtagag    180
ggaggcaccc tgggctgtgt atgaaaggcc aacttctccg ggcacatgta catcttaccc    240
cagggcgagt accctgaata ccagcgttgg atgggcctta atgaccgcct gggctcttgc    300
cgagctgttc atctgtctag cggaggccag gctaagattc aggtctttga aaagggcgac    360
ttcaacggtc agatgtacga aaccacggaa gactgtcctt ctatcatgga gcagtttcac    420
ctgcgagaga ttcattcctg taaggtggta gaaggcacct ggattttcta tgagctaccc    480
aactaccgtg gcagacagta tcttctggat aagaaggagt accggaagcc cgtcgattgg    540
```

```
ggtgcggcat cccccgctat ccagtcgttc cgccgcattg tggagtgatg gcctggagtg    600
ggaccataga gttctccctg agggctgaac ttgagggctg aactctgctg tctggcttgt    660
ggtccaaata gacaacgtaa taaaagcatt ggaatgcctc cc                       702
```

<210> SEQ ID NO 30
<211> LENGTH: 510
<212> TYPE: DNA
<213> ORGANISM: Mus musculus

<400> SEQUENCE: 30

```
ggaacaaatg caccagagaa aatcttggtt ttgaattttt taaacgtttg gctgggtttt     60
gggtgccttg attcagcaga gcctacaatg cagtagggct gggcgagcat tacaggggcc    120
acagagctct cctttatttc ataatcccaa ttgttttttct agcaaccatc aatagactct   180
aaatgactga ctcaaatttt ggatccaatt ctcatgacta gcagatgtt tgatttgaac     240 tgccctctat aaatgtccct ctgcctgtag tcctggagct gccctggatc tctctcagta    300
gtgcgggaat caacctttgc acatacaatg tctaaaactg gaggcaaggt aagtaactgt    360
ttctcatcca ggggcacgtt caaagcagag ctgttgcttc actgccctga gatgagtaaa    420
ctagtgctcg agggacaatc ctggggagag aagatggaaa aggcttgttt tctagtcaat    480
aaaacatcta cacacgttaa agattattgt                                     510
```

<210> SEQ ID NO 31
<211> LENGTH: 1608
<212> TYPE: DNA
<213> ORGANISM: Mus musculus

<400> SEQUENCE: 31

```
tcacagtaga aggaaagcca atctaattcg acagtgtgct tgtcgctttt atctgtgtgc     60
aaagccgccc agctcctcag ctcactcagt gctctgtgtg cagattagtt tctacgaaga    120
ccgaaatttt caaggccgcc gctatgactg cgactgcgac tgcgcagact ccgctcgta    180 cctaagtcgc tgcaactcca ttagagtaga gggaggcacc tgggctgtgt atgaaaggcc    240
caacttctcc gggcacatgt acatcttacc ccagggcgag taccctgaat accagcgttg    300
gatgggcctt aatgaccgcc tgggctcttg ccgagctgtt catctggtga gtctggaagc    360
ttgctatgtg gccacgaccc cgcatctttc cttcctttcg ttttttttgtt ttggttgttg    420 ttgttgtttg tttgtttct tgttttgttt taccaaaaca gggtttctct gtgttacact     480
ggctgtccca aaaactcact ttgtaatcag gctggccttg aactcagaaa tccgcctgcc    540
tctgcctccc aagtgctgga attaaaggcg tgtgctacca cgcctggcta aattttgttt    600
ttatgagtgt gtgtgtgtgt gtgtgtgtgt gtgtgtgtgt gtgtgtgtgt ttcgcacaca    660
tttgcatgca gtaccctcag aggctgggga agggtgttgg ctcctctaga gctggagtta    720
acaggcagat tagatatggg ctgctggatg gagcttttgg aactaactcg tatgttggta    780
gagctgcatg tacttaactg ttgagctatc tctccatcca ctcccgtctc cccacagccc    840
tttcctaagt cttcctacct cttcttcgtt gaatgaaata agaatcttag tttacttcat    900
cagtagacta aatggcatta cttttcagct cgtggctgag atcaagtaga gagtaaatac    960
tagttgttca aggactctct ctccctcata gatgtttatc gcaattgtgc tagtccaccc   1020 tttggtatt tcatggtggc aaccagagtt ctgatgaccc tcccttaagg atgagaggct    1080
gtgcaccaag ctgtccccga gttcctgaca tgctaatgat ttctgtaaca atggctgttc   1140
atttcttttt gttggtcttg ttcttgcttt cagtctagcg gaggccaggc taagattcag   1200
```

```
gtctttgaaa agggcgactt caacggtcag atgtacgaaa ccacggaaga ctgtccttct    1260
atcatggagc agtttcacct gcgagagatt cattcctgta aggtggtaga aggcacctgg    1320
attttctatg agctacccaa ctaccgtggc agacagtatc ttctggataa gaaggagtac    1380
cggaagcccg tcgattgggg tgcggcatcc cccgctatcc agtcgttccg ccgcattgtg    1440
gagtgatggc ctggagtggg accatagagt tctccctgag ggctgaactt gagggctgaa    1500
ctctgctgtc tggcttgtgg tccaaataga caacgtaaat aaaagcattg gaatgcatcc    1560
catcgttgac tattgtgcct cttcttaatt gcttttagga ccagcaat                1608
```

<210> SEQ ID NO 32
<211> LENGTH: 698
<212> TYPE: DNA
<213> ORGANISM: Homo sapiens

<400> SEQUENCE: 32

```
ctgaatttct ttcagcactg ggaaaaccag tctatgcacc aaaaatgtct aaaactggaa     60
ccaagattac tttctatgaa gacaaaaatt ttcaaggccg tcgctatgac tgtgattgcg    120
actgtgcaga tttccacaca tacctaagtc gctgcaactc cattaaagtg gaaggaggca    180
cctgggctgt ttatgaaagg cccaactttg ctgggtacat gtacatctta ccacagggag    240
agtaccctga ataccagcgt ggatgggcc tcaacgaccg cctcagctcc tgcagagctg     300
ttcatctgcc tagtggaggc cagtataaga ttcagatctt tgagaaaggg gattttagtg    360
gtcagatgta tgaaaccacc gaagattgcc cttccatcat ggagcaattt cacatgcgag    420
agatccactc ctgtaaggtg ctggagggtg tctggatttt ctatgagcta cccaactacc    480
gtggcaggca gtacctcctg acaagaagg agtaccggaa gcccatcgat tggggtgcag     540
cctccccagc tgtccagtct ttccgccgca ttgtggagta atgacatgaa tggggccata    600
ttcttcctgg ggcccaaatg ctggctgcc ttgtggtcca aataggcatc atcaataaaa      660
cagttggcat gcatcccaaa aaaaaaaaa aaaaaaaa                             698
```

<210> SEQ ID NO 33
<211> LENGTH: 11
<212> TYPE: DNA
<213> ORGANISM: Mus musculus

<400> SEQUENCE: 33

```
ccgtcgattg g                                                           11
```

<210> SEQ ID NO 34
<211> LENGTH: 11
<212> TYPE: DNA
<213> ORGANISM: Mus musculus

<400> SEQUENCE: 34

```
ccgtcgattg a                                                           11
```

<210> SEQ ID NO 35
<211> LENGTH: 11
<212> TYPE: DNA
<213> ORGANISM: Mus musculus
<220> FEATURE:
<221> NAME/KEY: misc_feature
<222> LOCATION: (3)..(9)
<223> OTHER INFORMATION: n is a, c, g, or t

<400> SEQUENCE: 35

```
ccnnnnnnng g                                                             11

<210> SEQ ID NO 36
<211> LENGTH: 10
<212> TYPE: DNA
<213> ORGANISM: Mus musculus

<400> SEQUENCE: 36
aaactactgc                                                               10

<210> SEQ ID NO 37
<211> LENGTH: 10
<212> TYPE: DNA
<213> ORGANISM: Mus musculus
<220> FEATURE:
<221> NAME/KEY: misc_feature
<222> LOCATION: (7)..(7)
<223> OTHER INFORMATION: n is a, c, g, or t

<400> SEQUENCE: 37 aaactantgc                                                               10

<210> SEQ ID NO 38
<211> LENGTH: 10
<212> TYPE: DNA
<213> ORGANISM: Mus musculus

<400> SEQUENCE: 38
aaactagtgc                                                               10

<210> SEQ ID NO 39
<211> LENGTH: 21
<212> TYPE: DNA
<213> ORGANISM: Mus musculus

<400> SEQUENCE: 39
gggagcttgc tatgtatgtg g                                                  21

<210> SEQ ID NO 40
<211> LENGTH: 21
<212> TYPE: DNA
<213> ORGANISM: Mus musculus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t

<400> SEQUENCE: 40
ggnagcttgc tatgtnnnnn n                                                  21

<210> SEQ ID NO 41
<211> LENGTH: 21
<212> TYPE: DNA
<213> ORGANISM: Mus musculus

<400> SEQUENCE: 41
ggaagcttgc tatgtggcca c                                                  21

<210> SEQ ID NO 42
<211> LENGTH: 10
<212> TYPE: DNA
<213> ORGANISM: Mus musculus
```

```
<400> SEQUENCE: 42
ttgaggtgcg                                                              10

<210> SEQ ID NO 43
<211> LENGTH: 10
<212> TYPE: DNA
<213> ORGANISM: Mus musculus

<400> SEQUENCE: 43
ttgaggtgcg                                                              10

<210> SEQ ID NO 44
<211> LENGTH: 11
<212> TYPE: DNA
<213> ORGANISM: Mus musculus
<220> FEATURE:
<221> NAME/KEY: misc_feature
<222> LOCATION: (4)..(4)
<223> OTHER INFORMATION: n is a, c, g, or t

<400> SEQUENCE: 44
ttgnggtgcg g                                                            11

<210> SEQ ID NO 45
<211> LENGTH: 10
<212> TYPE: DNA
<213> ORGANISM: Mus musculus

<400> SEQUENCE: 45
ttggggtgcg                                                              10
```

METHOD OF DIAGNOSING AND TREATING LESION OF CRYSTALLINE LENS USING HUMAN CRYGS GENE AND CODING PRODUCT THEREOF

FIELD OF INVENTION

This invention relates to both biological engineering and medical fields. In particular, it relates to a method of diagnosing and treating lens illnesses using human CRYGS gene and the coded product, and a pharmaceutical composition containing CRYGS gene and/or protein.

TECHNICAL BACKGROUND

Cataract is a common eye disease, one of the leading causes of human blindness and one of the main diseases that severely influence the people's life. The main cause of cataract is the degeneration or sedimentation of crystallin in the lens. There are three kinds of crystallin: α-crystalline, β-crystalline, γ-crystallin. The γ-crystallin family consists of 7 members: A, B, C, D, E, F, S-crystallin. The previous reports show that the change of some crystallins may cause the lens illness and cataract. However, the mechanism of cataract is still unclear so far. Also the relationship between cataract and some special kind of crystallin is not reported.

Further, there is still no effective method to diagnose cataract early and to cure cataract by non-operative treatment in the art.

Therefore, there is an urgent need to develop new and efficient methods to diagnose and cure cataract, the relative pharmaceuticals, and diagnostic technology and reagents.

SUMMARY OF INVENTION

One purpose of the invention is to provide a new diagnostic method, especially for early diagnosis, and detection kit for cataract and other lens illnesses.

Another purpose is to provide a new method to treat cataract and other lens illnesses.

Still another purpose is to provide a pharmaceutical composition to treat cataract and other lens illnesses.

In the first aspect, the invention provides a method for determining the cataract susceptibility in a subject comprising the steps of:
  detecting the CRYGS gene, transcript and/or protein in said subject and comparing it with the normal CRYGS gene, transcript and/or protein to determine whether there is any difference, wherein said difference indicates that the possibility of suffering cataract in said subject is higher than the normal population.

In a preferred embodiment, the CRYGS gene or transcript is detected, and compared with the normal CRYGS nucleotide sequence to determine the difference. More preferably, said difference is selected from the group consisting of: in position 76 of Intron 1, G76→C76; in position 11 of Intron 2, A11→G11; in position 24 of Intron 2, ATGT is repeated; and in position 489 of mRNA encoding sequence or Exon 3, G489→A489.

In the second aspect, the invention provides a method for treating lens illnesses comprising the step of administrating a safe and effective amount of normal CRYGS protein to the patient in need of said treatment. Preferably, the CRYGS protein is administrated topically to the eyes.

In the third aspect, the invention provides a pharmaceutical composition comprising a safe and effective amount of CRYGS protein and a pharmaceutically acceptable carrier. Preferably, said pharmaceutical composition is eyedrops or eye ointments.

In the fourth aspect, the invention provides a kit for detecting lens illnesses comprising the primers which specifically amplify the CRYGS gene or transcript. Preferably, the kit further comprises a probe that binds to the site of mutation.

In view of the technical teaching of the invention, the other aspects of the invention will be apparent to the skilled in the art.

DESCRIPTION OF DRAWINGS

FIGS. 3A-C show the sequence mutation in Crygs gene.

DETAILED DESCRIPTION OF INVENTION

People have a limited knowledge about γS-crystallin (in short, "CRYGS") which is one kind of crystallins, and do not know whether it is relevant to cataract. The inventors of the invention have for the first time found out and proved that this crystallin has a close relationship with cataract. In addition, the new function of CRYGS that the changes of γS-crystallin will cause the lens illnesses and cataract is discovered. Based on this discovery, the inventors accomplished the invention.

The inventors established an autosomal recessive cataract mouse model. The mutation of γS-crystallin causes the mouse suffering from the lens lesion and cataract. The cataract locus of rncat mouse model was mapped onto the Chromosome 16 by AFLP, RH Panel, STR Markers and other methods. It is found that the Crygs gene mutation located at 16cM on mouse Chromosome 16 is relative to cataract by the SSCP analysis. Our study suggests that mouse Crygs protein is closely related to cataract and is involved in the regulation of epithelial cell development, differentiation, proliferation and stabilization. The stable presence of mouse Crygs is key to maintain the normal physiological state of lens. The mutation of γS-crystallin is one of the direct causes for lens illnesses, such as cataract.

By comparing the protein homology, we have found human γS-crystallin (CRYGS) shared a high homology with mouse Crygs (identity=160/178, 89%; similiarity=172/178, 95%). This result suggests that we can find the counterparts in human for those changes in mouse Crygs gene and the resultant physiological changes. So the mutation of human CRYGS can also lead to the lens illnesses in human. Based on the CRYGS gene and its expression products, one can develop new drugs and diagnosis/treatment techniques for detecting and treating human lens illnesses.

The CRYGS protein or polypeptide have various uses including but not limited to: curing disorders caused by low or no activity of CRYGS protein (using directly as a medicine), and screening out antibodies, polypeptides or ligands which promote the function of CRYGS. The expressed recombinant CRYGS protein can be used to screen polypeptide library to find therapeutically valuable polypeptide molecules which activate the function of CRYGS protein.

In another aspect, the invention also includes polyclonal and monoclonal antibodies, preferably monoclonal antibodies, which are specific for polypeptides encoded by human CRYGS DNA or fragments thereof. By "specificity", it is meant an antibody which binds to the human CRYGS gene products or a fragments thereof. Preferably, the antibody binds to the human CRYGS gene products or fragments thereof and does not substantially recognize nor bind to other antigenically unrelated molecules. Antibodies which bind to human CRYGS and block human CRYGS protein and those which do not affect the human CRYGS function are included in the invention.

The present invention includes not only intact monoclonal or polyclonal antibodies, but also immunologically-active antibody fragments, e.g., a Fab' or (Fab)$_2$ fragment, an antibody heavy chain, an antibody light chain, a genetically engineered single chain Fv molecule (Lander, et al., U.S. Pat. No. 4,946,778), or a chimeric antibody, e.g., an antibody which contains the binding specificity of a murine antibody, but the remaining portion of which is of human origin.

The antibodies in the present invention can be prepared by various techniques known to those skilled in the art. For example, purified human CRYGS gene products, or its antigenic fragments can be administrated to animals to induce the production of polyclonal antibodies. Similarly, cells expressing human CRYGS or its antigenic fragments can be used to immunize animals to produce antibodies. The antibodies of the invention can be monoclonal antibodies which can be prepared by using hybridoma technique (See Kohler, et al., Nature, 256; 495,1975; Kohler, et al., Eur. J. Immunol. 6: 511,1976; Kohler, et al., Eur. J. Immunol. 6: 292, 1976; Hammerling, et al., In Monoclonal Antibodies and T Cell Hybridomas, Elsevier, N.Y., 1981). Antibodies of the invention comprise those which block human CRYGS function and those which do not affect human CRYGS function. Antibodies in the invention can be produced by routine immunology techniques and using fragments or functional regions of human CRYGS gene product. These fragments and functional regions can be prepared by recombinant methods or synthesized by a polypeptide synthesizer. The antibodies binding to unmodified human CRYGS gene product can be produced by immunizing animals with gene products produced by prokaryotic cells (e.g., E. coli), and the antibodies binding to post-translationally modified forms thereof can be acquired by immunizing animals with gene products produced by eukaryotic cells (e.g., yeast or insect cells).

The antibody against human CRYGS protein can be used in immunohistochemical method to detect the presence of CRYGS protein in the biopsy specimen.

The polyclonal antibodies can be prepared by immunizing animals, such as rabbit, mouse, and rat, with human CRYGS protein. Various adjuvants, e.g., Freund's adjuvant, can be used to enhance the immunization.

The substances which act with CRYGS protein, e.g., inhibitors, agonists and antagonists, can be screened out by various conventional techniques, using the protein of the invention.

The protein, antibody, inhibitor, agonist or antagonist of the invention provide different effects when administrated in therapy. Usually, these substances are formulated with a nontoxic, inert and pharmaceutically acceptable aqueous carrier. The pH typically ranges from 5 to 8, preferably from about 6 to 8, although pH may alter according to the property of the formulated substances and the diseases to be treated. The formulated pharmaceutical composition is administrated in conventional routine including, but not limited to, intramuscular, intravenous, subcutaneous, or topical administration including circumocular, retrobulbar and intraocular injection. The topical administration at eyes is preferred.

The normal CRYGS can be directly used for curing disorders, e.g., lens illnesses including cataract. The CRYGS protein of the invention can be administrated in combination with other cataract medicaments.

The invention also provides a pharmaceutical composition comprising safe and effective amount of CRYGS protein in combination with a suitable pharmaceutical carrier. Such a carrier includes but is not limited to saline, buffer solution, glucose, water, glycerin, ethanol, or the combination thereof. The pharmaceutical formulation should be suitable for the delivery method. The pharmaceutical composition of the invention may be in the form of injections which are made by conventional methods, using physiological saline or other aqueous solution containing glucose or auxiliary substances. The pharmaceutical compositions in the form of eyedrops, eye ointments, tablet or capsule may be prepared by routine methods. The pharmaceutical compositions, e.g., eyedrops, eye ointments, injections, solutions, tablets, and capsules, should be manufactured under sterile conditions. The active ingredient is administered in therapeutically effective amount, e.g., from about 1 ug to 5 mg per kg body weight per day. Moreover, the polypeptide of the invention can be administrated together with other therapeutic agents.

When using pharmaceutical composition, the safe and effective amount of the CRYGS protein or its antagonist or agonist is administrated to mammals. Typically, the safe and effective amount is at least about 0.1 ug/kg body weight and less than about 10 mg/kg body weight in most cases, and preferably about 0.1-100 ug/kg body weight. Of course, the precise amount will depend upon various factors, such as delivery methods, the subject health, and the like, and is within the judgment of the skilled clinician.

The human CRYGS polynucleotides also have many therapeutic applications. Gene therapy technology can be used in the therapy of abnormal cell proliferation, development or metabolism, which is caused by the loss of CRYGS expression or the expression of abnormal or non-active CRYGS. The methods for constructing a recombinant virus vector harboring CRYGS gene are described in the literature (Sambrook, et al.). In addition, the recombinant CRYGS gene can be packed into liposome and then transferred into the cells.

The methods for introducing the polynucleotides into tissues or cells include: directly injecting the polynucleotides into tissue in the body, in vitro introducing the polynucleotides into cells with vectors, such as virus, phage, or plasmid, and then transplanting the cells into the body.

The invention further provides diagnostic assays for quantitative and in situ measurement of CRYGS protein level. These assays are well known in the art and include FISH assay and radioimmunoassay. The level of CRYGS protein detected in the assay can be used to illustrate the importance of CRYGS protein in diseases and to determine the diseases associated with CRYGS protein.

A method of detecting the presence of CRYGS protein in a sample by utilizing the antibody specifically against CRYGS protein comprises the steps of: contacting the sample with the antibody specifically against CRYGS protein; observing the formation of antibody complex which indicates the presence of CRYGS protein in a sample.

The polynucleotide encoding CRYGS protein can be used in the diagnosis and treatment of CRYGS protein related diseases. In respect of diagnosis, the polynucleotide encoding CRYGS can be used to detect whether CRYGS is expressed or not, and whether the expression of CRYGS is normal or abnormal, e.g., in the case of diseases. CRYGS DNA sequences can be used in the hybridization with biopsy samples to determine the expression of CRYGS. The hybridization methods include Southern blotting, Northern blotting and in situ blotting, etc., which are public and sophisticated techniques. The corresponding kits are commercially available. A part of or all of the polynucleotides of the invention can be used as probe and fixed on a microarray or DNA chip for analyzing the differential expression of genes in tissues and for the diagnosis of genes. The CRYGS specific primers can be used in RNA-polymerase chain reaction and in vitro amplification to detect the transcripts of CRYGS.

Further, detection of the mutation of CRYGS gene is useful for the diagnosis of CRYGS protein related diseases. The mutation forms of CRYGS include site mutation, translocation, deletion, rearrangement and any other mutations compared with the normal wild-type CRYGS DNA sequence. The conventional methods, such as Southern blotting, DNA sequencing, PCR and in situ blotting, can be used to detect mutation. Moreover, mutation sometimes affects the expression of protein. Therefore, Northern blotting and Western blotting can be used to indirectly determine whether the gene is mutated or not.

The invention is further illustrated by the following examples. It is appreciated that these examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

In this invention, the CRYGS sequence and other helpful information can be found in the following electric database.

Mouse genome Informatics, MGI. (The marker sequences and genetic sites)

Whitehead Institute/MIT Center for Genome Research. (About RH mapping)

Genbank overview, (mouse Crygs [AF032995 SE ID NO:29, AF055702 (SEQ ID NO:30 and AF055703 SEQ ID NO:31)] and human CRYGS [AF161703 SEQ ID NO:32 1)]).

EXAMPLE 1

Establishing Model Animal and DNA Samples

The autosomal recessive cataract mutation arose spontaneously in a KUNMING outbred mouse strain. We maintained the mice by sib mating. After more than 20 generations of sib mating for ten years, the mutant mice were stabilized and formed an independent strain—autosomal recessive cataract mice model (rncat). Cataract model mice (rncat) is an autosomal recessive cataract model which is an independent strain after 20 generations of sib mating for ten years. The cataract develops spontaneously during propagation.

Figure 1A:
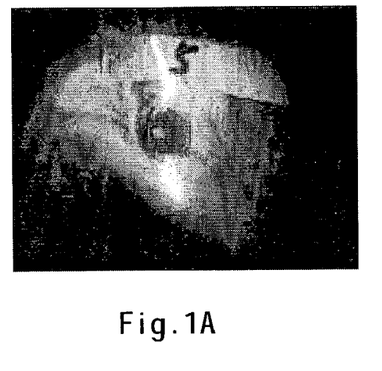
FIGS. 1A-C show pathological changes in the eyes of cataract mouse model.
Figure 1B:
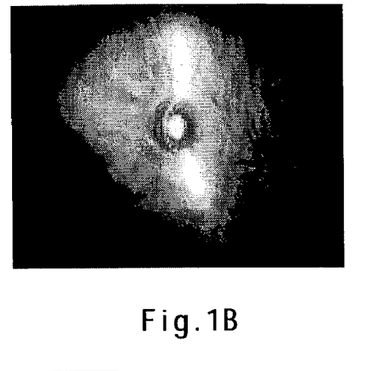
Figure 1C:
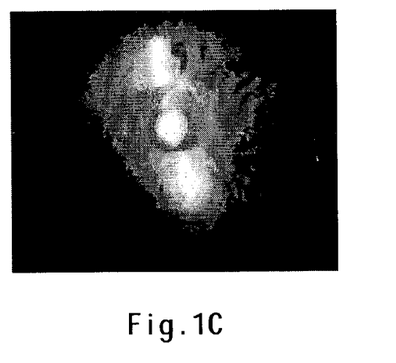
Figure 2A:
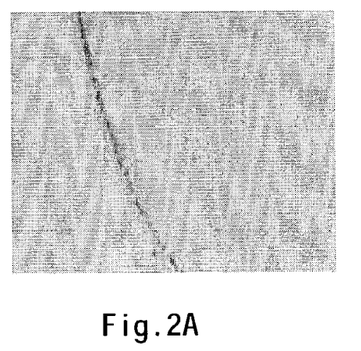
FIGS. 2A-2F show the pathological changes of the lens.
Figure 2B:
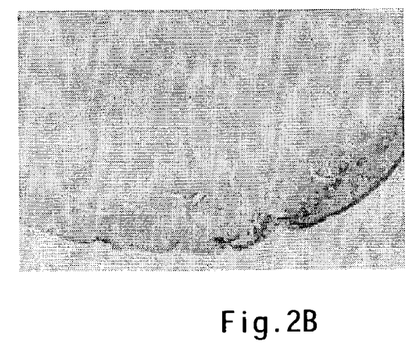
Figure 2C:
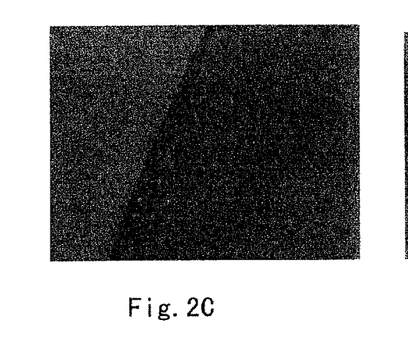
Figure 2D:
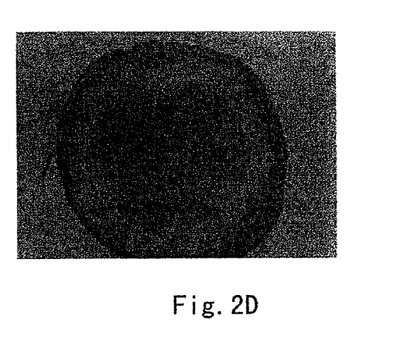
Figure 2E:
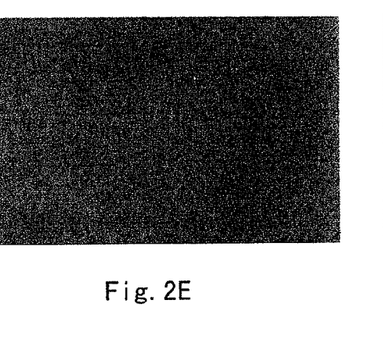
Figure 2F:
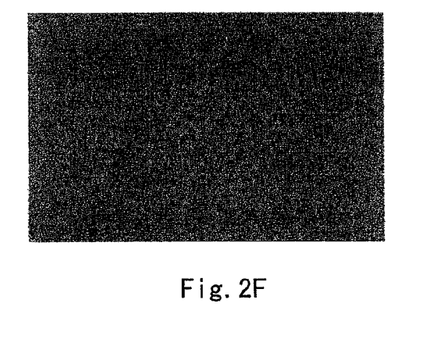

The development of cataract in rncat mouse is a progressive process (FIGS. 1A-1C). The lens is transparent during 0 to 10 days and the mist-shaped white can be observed during 10 to 15 days (FIG. 1A). During 15 to 30 days, the cataract is matured gradually to form a typical nuclear cataract (FIGS. 1B, and 1C).

In genetic analysis, the cataract mice were crossed to the inbred line of B10SN mice to generate F1 hybrids, which were further backcrossed to the mutant mice to generate F2 mice. Hence, there were two phenotypes in F2 mice lenses: normal and cataract.

The DNA samples for genetic analysis were prepared from liver tissues of 40 days old F2 mice.

Mapping rncat Locus

Initially, amplified fragment length polymorphism analysis (AFLP) was performed to map the rncat locus.

The genomic DNA of F2 mice was digested with EcoRI/MseI or EcoRI/TaqI. Then, the corresponding adapters were linked to the ends of the digested fragments.

```
Eco RI adapter
5'-CTCGTAGACTGCGTACC           (SEQ ID NO: 1)
    CATCTGACGCATGGTTAA-5'      (SEQ ID NO: 2)

Mse I adapter
5'-GACGATGAGTCCTGAG            (SEQ ID NO: 3)
        TACTCAGGACTCAT-5'      (SEQ ID NO: 4)

Taq I adapter
5'-GACGATGAGTCCTGAG            (SEQ ID NO: 5)
        TACTCAGGACTCGC-5'      (SEQ ID NO: 6)
```

After overnight linkage at 16° C., the linkage products were diluted 10 times and pre-amplified with the primers of EcoRI and Mse I combination, or of Eco RI and Taq I combination.

```
Eco RI pre-amplification primer (EcoRI-C)
5'-GACTGCGTACCAATTCC-3'     (SEQ ID NO: 7)

Mse I pre-amplification primer (Mse I-C)
5'-GATGAGTCCTGAGTAAC-3'     (SEQ ID NO: 8)

Taq I pre-amplification primer (Taq I-A)
5'-GATGAGTCCTGAGCGAA-3'     (SEQ ID NO: 9)
```

After the standard pre-amplification, the PCR products were diluted 10 times and amplified in a selective amplification with Eco RI and Mse I selective amplification primers, or Eco RI and Taq I selective amplification primers. An M13 operon sequence was added to the 5' end of EcoRI selective primer to facilitate the detection by the Li-Cor Automated Sequencer. After selective amplification, the PCR products were separated on denaturing polyacrylamide gel and detected on an automatic Fluorescent sequencer. The selective EcoRI-primer was modified by adding an M13 tail to facilitate detection by the Li-Cor IR$^2$ Automated Sequencer.

AFLP selective EcoRI-primers are as follows:

```
EcoRI selective amplification primer (Eco RI-CAN)
                                      (SEQ ID NO: 10)
5'-CACGACGTTGTAAAACGACTGCGTACCAATTCCAN-3'

Mse I selective amplification primer (Mse I-CNN)
                                      (SEQ ID NO: 11)
5'-GATGAGTCCTGAGTAACNN-3'

Taq I selective amplification primer (Taq I-ANN)
                                      (SEQ ID NO: 12)
5'-GATGAGTCCTGAGCGAANN-3'

(wherein N is A, T, C or G).
```

We found that, in the fragments amplified by EcoRI-CAC and Taq I-ACT selective amplification primers, there was a fragment linked to the cataract phenotype. This fragment was labeled with isotope, re-amplified, recovered from denaturing polyacrylamide gel and sequenced. Based on the sequencing results, the following primers were designed:

```
Forward primer:
5'-CATTTTCATGTCTAAGCCAG-3';  (SEQ ID NO: 13)
```

-continued

Reverse primer:
5'-AGAGTGAAATGGATCAGATG-3'.      (SEQ ID NO: 14)

The fragment was mapped onto mouse Chromosome 16 and close to microsatellite marker D16Mit39 (LOD>3) by using PCR-based Mouse Radiation Hybrid Panel (Research Genetics Inc. Huntsville, Ala., USA) and the above primers.

Based on the above results, six microsatellite markers, D16Mit129, D16Mit9, D16Mit60, D16Mit59, D16Mit158 and D16Mit6, were further used to narrow down the rncat locus. As a result, the gene causing mouse cataract was located between microsatellite markers D16Mit9 and D16Mit60.

Screening Candidate Genes and Detecting Mutations

In the above location, Cryge gene is an important candidate gene which specifically expressed in the eye and highly expressed at lens. We designed seven pairs of primers covering all the exons, intron/exon boundaries and some operon sequences of Crygs:.

```
Crygs-1 F,
5'-TAGGGCTGGGCGAGCATTAC-3';       (SEQ ID NO: 15)

Crygs-1 R;
5'-CAAAGGTTGATTCCCGCACT-3';       (SEQ ID NO: 16)

Crygs-2 F,
5'-GTCCCTCTGCCTGTAGTCCT-3';       (SEQ ID NO: 17)

Crygs-2 R;
5'-ACAAGCCTTTTCCATCTTCTC-3';      (SEQ ID NO: 18)

Crygs-3 F,
5'-CCAGCTCCTCAGCTCACTCA-3';       (SEQ ID NO: 19)

Crygs-3 R;
5'-CCATCCAACGCTGGTATTCA-3';       (SEQ ID NO: 20)

Crygs-4 F,
5'-CCGCTCGTACCTAAGTCGCT-3';       (SEQ ID NO: 21)

Crygs-4 R;
5'-AGGAAAGATGCGGGGTCGTG-3';       (SEQ ID NO: 22)

Crygs-5 F,
5'-CCGAGTTCCTGACATGCTAA-3';       (SEQ ID NO: 23)

Crygs-5 R;
5'-ATACTGTCTGCCACGGTAGTT-3';      (SEQ ID NO: 24)

Crygs-6 F,
5'-GAGATTCATTCCTGTAAGGTGGTA-3';   (SEQ ID NO: 25)

Crygs-6 R;
5'-CCTCAGGGAGAACTCTATGGTC-3';     (SEQ ID NO: 26)

Crygs-7 F,
5'-TCTGGATAAGAAGGAGTACCG-3';      (SEQ ID NO: 27)

Crygs-7 R;
5'-GGTCCTAAAAGCAATTAAGAAG-3'.     (SEQ ID NO: 28)
```

Figure 3A:
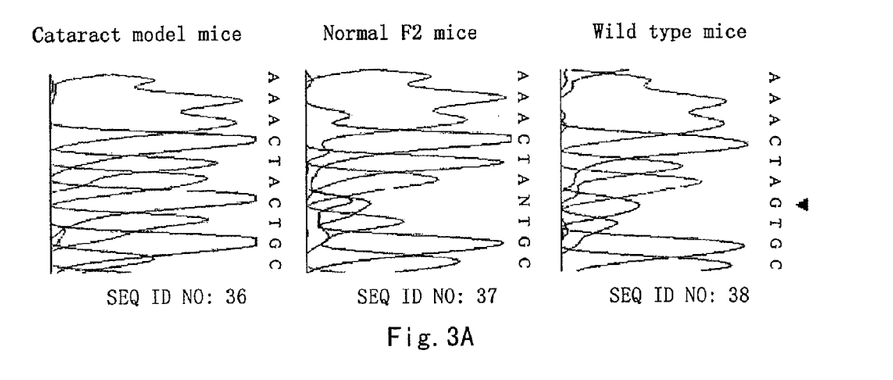
FIG. 3A shows a G76→C76 substitution at nt76 in Intron 1(SEQ ID NOs: 36-38).
Figure 3B:
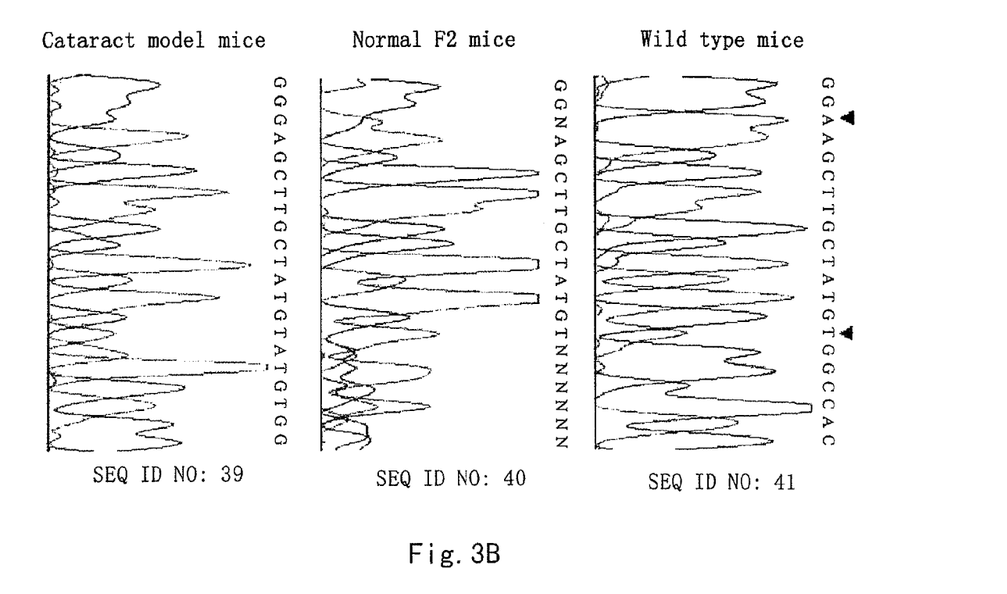
FIG. 3B shows an A11→G11 substitution at nt11 in Intron 2 and a 4 bp repetition (ATGT) at position 24 in Intron 2(SEQ ID NOs: 39-41).
Figure 3C:
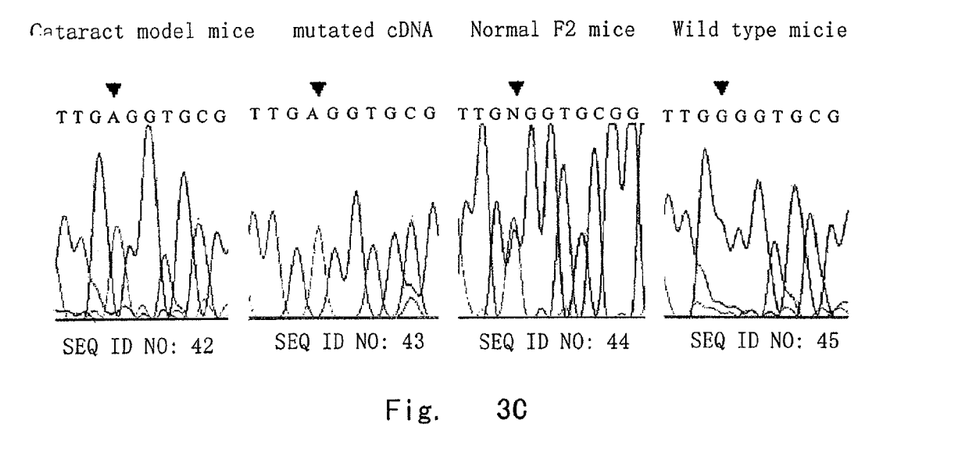
FIG. 3C shows a G489→A489 substitution at position 489 in the mRNA encoding sequence or Exon 3(SEQ ID NOs42-45).

Using these seven pairs of primers and SSCP analysis, the mutation of Crygs gene in our cataract model mice was detected. Four pairs of primers, Crygs-2, Crygs-4, Crygs-6, and Crygs-7, detected the Crygs gene of cataract mice was different from that of normal mice. The sequence results showed that Crygs-6 and Crygs-7 detected the mutation in the same site. Crygs-2 corresponded to Intron 1. Crygs-4 corresponded to Intron 2. Crygs-6 and 7 corresponded to Exon 3. The mutations detected on an automatic sequencer were as follows (FIG. 3):

a G76→C76 substitution at nt76 in Intron 1.( FIG. 3A)

an A11→G11 substitution at nt11 in Intron 2 and a 4 bp repetition (ATGT) at position 24 in Intron 2 (FIG. 3B)

a G489→A489 substitution at position 489 in the mRNA encoding sequence or Exon 3 (FIG. 3C).

The sequencing of Crygs transcript of rncat mice also showed the mutation of G489→A489 which changed sequence from $CC_{GTCGATT}GG$ (SEQ ID NO:33)into $CC_{GTCGATT}GA$. This mutation results in the loss of a BsII site of $CCN_7GG$ (SEQ ID NO: 35). In the detection of enzyme digestion, the mutant is not recognized by BsII and, thus, not digested because of said mutation.

The G489→A489 mutation changes the amino acid Trp163 in Cryge protein into a stop codon. Therefore, the Crygs protein consisting of 178 amino acids is changed into a mutant having 162 amino acids. This change directly causes mice to exhibit cataract and pathological changes of lens (FIGS. 2A-F):

The lens epithelial cells are exceedingly proliferated and differentiated. Vacuoles are formed.

Cortex fibers are denaturalization underneath the posterior lens and completely disordered. Calcium-dots and blue-stained spherical bodies are seen;

The embryonic nucleus of the lens is highly pink stained.

These pathological symptoms are the same as those in human.

Results and Discussion

Clinical Features of the Mutant (rncat) Mice.

Opacity of the lens appeared 11 days after birth and progressed with age (FIGS. 1A, 1B, and 1C). Slit lamp examination showed that the opacity remained concentrated in the nuclear region in homozygous mutant mice while the lenses of heterozygous mice remained normal. Histological examinations of epithelial lens cells showed a notable degeneration and loss of proper junction. Epithelial cells in the equatorial region seemed to over proliferate and displayed a reduced potential for differentiation. The proliferative cells appeared to migrate extensively towards the anterior and posterior poles. Although Crygs is expressed in retina, retina cells appear normal in morphology. In the cortical area underneath the posterior lens capsule, vacuoles and Morgagnian-like bodies were seen, while in the nucleus of the lens, blue-stained spherical bodies form an unusual Y-like pattern. The lens fibers seemed to have lost their normal orientations while the central region of the lens appeared pink compared to the outer cortex region. Except for the lens abnormalities described here, no other morphological or behavioral abnormalities were observed in the mutant mice.

Genetic Localization of the rncat Locus.

In order to identify the gene responsible for the defect, we performed a genome-wide search using amplified fragment length polymorphism (AFLP) markers initially on 6 mutants and 5 wild-type F2 mice. A polymorphic band associated with cataract was identified in the 11 mice tested. To confirm this association, 20 additional F2 mice were subjected to genotyping analysis and consistent results were obtained. In order to map the polymorphic band in the mouse genome, we sequenced these polymorphic PCR products. PCR primers were then designed based on sequencing results and were used to screen a mouse radiation hybrid panel so as to locate the position on chromosomes. To further locate the cataract locus, we genotyped 191 F2 mice using 6 microsatellite markers in 3.3-45.9 cM and mapped the rncat locus to the interval between 4.4 cM and 25.1 cM of chromosome 16. The candidate gene, γS-crystallin or Crygs gene was located in this region.

Mutation Analysis of Crygs Gene.

Mouse Crygs gene sequence is available from Genbank database. For mutation analysis, we performed a single strand conformation polymorphisms analysis (SSCP). From the sequencing results, interestingly, a G→C substitution at position 76 of Intron 1, an A→G substitution at position 11 of Intron 2, and an ATGT insertion at position 24 of Intron 2 were also identified in the mutant mice. Surprisingly, among 10 different outbred mouse strains with wild-type phenotype, we found G489A substitution and no other mutation in these two introns. If the G489A substitution in this mouse has the same origin as in the cataract mutant mice, the intron mutations must have arisen after the G489A substitution.

Discussion.

The γS-crystallin protein encoded by the Crygs gene is folded into four β-sheet motifs, which are organized into two domains. The G489A mutation may interrupt the formation of the C-terminal domain. Sequence alignment indicates that the Trp163 is a highly conserved amino acid residue among γ-crystallin members in mouse and other species, suggesting that Trp163 may be essential for the normal function of γS-crystallin. In vitro, γS-crystallin plays an important role in suppressing the aggregation of other γ-crystallins and in interacting with α-crystallin. The truncated γS-crystallins may lose normal functions with other molecules or cause themselves insoluble.

In the mutant mice, the pink stained nucleus in the central region of the lens suggests a lower pH value in the nucleus compared to the outer cortex region, and may be a result of the aggregation of acid molecules. Because γS-crystallin gene mainly expresses in the secondary lens fiber cells, most of which are in nucleus, we postulate that most of the aggregated molecules in the nucleus are not the truncated γS-crystallins but other proteins. Analysis of histological results indicates that the truncated γS-crystallin promotes the proliferation and migration of epithelial cells, and a disorder in lens fiber architecture in mutant mice is readily observed. This suggests that γS-crystallin may be involved in epithelial cell growth and migration, which in turn may contribute to lens fiber organization. Additionally, epithelial cell degeneration and disjunction may result from the cellular toxic effect of the truncated γS-crystallin.

Crygs expression is not limited to the lens but is also present in the retina, cornea and some tumor tissues, suggesting multiple functions of the γS-crystallin protein in development and pathogenesis. It is unclear if the G489A mutation affects the physiology of retina and cornea. Histological examination has showed no obvious morphological abnormalities in retina cells in mutant mice. The expression of Crygs gene remains high until 7 days after death in mouse. From our materials, expression of Crygs gene is early-onset and high in mutant mice. The γS-crystallin absorbs ultraviolet as well as short wave blue radiation, thereby protecting the retina against photic damage. Crygs gene might play a similar role in the lens as that in the retina.

Overall, the study of this invention plays an important role in improve the molecular mechanism research of cataract and lens development.

All the documents cited herein are incorporated into the invention as reference, as if each of them is individually incorporated. Further, it would be appreciated that, in the above teaching of the invention, the skilled in the art could make certain changes or modifications to the invention, and these equivalents would still be within the scope of the invention defined by the appended claims of the present application.

References:

Berry V, Francis P, Kaushal S, Moore A, Bhattacharya S (2000) Missense mutations in MIP underlie autosomal dominant 'polymorphic' and lamellar cataracts linked to 12q. Nat Genet 25:15-17.

Bours J (1996) Calf lens alpha-crystallin, a molecular chaperone, builds stable complexes with beta s- and gamma-crystallins. Ophthalmic Res 28 Suppl 1:23-31.

Everett C A, Glenister P H, Taylor D M, Lyon M F, Kratochvilova-Loester J, Favor J (1994) Mapping of six dominant cataract genes in the mouse. Genomics 20:429-434.

Francis P J, Berry V, Moore A T, Bhattacharya S (1999) Lens biology: development and human cataractogenesis. Trends Genet 15:191-196.

Harding, J. J., Crabbe, M. J. C (1984) The lens: development, proteins, metabolism and cataract. In: Davson H, editor. The eye, vol 1b. New York: Academic Press; 1984. P.207-492.

Hejtmancik J F (1998) The genetics of cataract: our vision becomes clearer. Am J Hum Genet 62:520-525

Jaworski C, Wistow G (1996) LP2, a differentiation-associated lipid-binding protein expressed in bovine lens. Biochem J 320 ( Pt 1):49-54.

Jones S E, Jomary C, Grist J, Makwana J, Neal M J (1999) Retinal expression of gamma-crystallins in the mouse. Invest. Ophthalmol Vis Sci 40:3017-3020.

Kerscher S, Glenister P H, Favor J, Lyon M F (1996) Two new cataract loci, Ccw and To3, and further mapping of the Npp and Opj cataracts in the mouse. Genomics. 36:17-21.

Knorr C, Cheng H H, Dodgson J B (1999) Application of AFLP markers to genome mapping in poultry. Anim Genet 30:28-35.

Lambert S R, Drack A V (1996) Infantile cataracts. Surv Ophthalmol. 40:427-458.

Liu C, Pande J, Lomakin A, Ogun O, Benedek G B (1998) Aggregation in aqueous solutions of bovine lens gamma-crystallins: special role of gamma(s). Invest Ophthalmol Vis Sci 39(9):1609-1619.

Mackay D, Ionides A, Kibar Z, Rouleau G, Berry V, Moore A, Shiels A et al. (1999) Connexin46 mutations in autosomal dominant congenital cataract. Am J Hum Genet 64:1357-1364

Quax-Jeuken Y, Driessen H, Leunissen J, Quax W, de Jong W, Bloemendal H (1985) beta s-Crystallin: structure and evolution of a distinct member of the beta gamma-superfamily. EMBO J 4:2597-2602.

Roll B (2000) Carotenoid and retinoid—two pigments in a gecko eye lens. Comp Biochem Physiol A Mol Integr Physiol 125:105-112.

Semina E V, Ferrell R E, Mintz-Hittner H A, Bitoun P, Alward W L, Reiter R S, Funkhauser C et al. (1998) A novel homeobox gene PITX3 is mutated in families with autosomal-dominant cataracts and ASMD. Nat Genet 19:167-170.

Shiels A, Bassnett S. (1996) Mutations in the founder of the MIP gene family underlie cataract development in the mouse. Nat Genet 12:212-215.

Shiels A, Mackay D, Ionides A, Berry V, Moore A, Bhattacharya S (1998) A missense mutation in the human connexin50 gene (GJA8) underlies autosomal dominant "zonular pulverulent" cataract, on chromosome 1q. Am J Hum Genet 62:526-532.

Sinha D, Esumi N, Jaworski C, Kozak C A, Pierce E, Wistow G (1998) Cloning and mapping the mouse Crygs gene and non-lens expression of [gamma]S-crystallin. Mol Vis 4:8.

Straatsma B R, Horwitz J, Takemoto L J, Lightfoot D O, Ding L L (1984) Clinicobiochemical correlations in aging-related human cataract. The Pan American Association and American Journal of Ophthalmology lecture. Am J Ophthalmol 97:457-469.

van Rens G L, Raats J M, Driessen H P, Oldenburg M, Wijnen J T, Khan P M, de Jong W W, Bloemendal H (1989) Structure of the bovine eye lens gamma s-crystallin gene (formerly beta s). Gene 78:225-233.

Voorter C E, De Haard-Hoekman W A, Hermans M M, Bloemendal H, De Jong W W (1990) Differential synthesis of crystallins in the developing rat eye lens. Exp Eye Res 50:429-437.

Vos P, Hogers R, Bleeker M, Reijans M, van de Lee T, Hornes M, Frijters A et al. (1995) AFLP: a new technique for DNA fingerprinting. Nucleic Acids Res 23:4407-4414.

Wistow G, Sardarian L, Gan W, Wyatt M K (2000) The human gene for gammaS-crystallin: alternative transcripts and expressed sequences from the first intron. Mol Vis 6:79-84.

Zarina S, Abbasi A, Zaidi Z H (1992) Primary structure of beta s-crystallin from human lens. Biochem J 287 ( Pt 2):375-381.

What is claimed is:

1. A method for determining the cataract susceptibility in a subject comprising the steps of:
   a) obtaining a biological sample from said subject, said biological sample comprising nucleic acids from the subject;
   b) detecting in said nucleic acids the subject's gamma-S crystalline (CRYGS) gene and determining the nucleic acid sequence of the subject's gamma-S crystalline (CRYGS) gene;
   c) detecting in the nucleic acid sequence of the subject's gamma-S crystalline (CRYGS) gene homozygous nucleotide content comprising:
      i) a C at position 424 of SEQ ID NO: 30 resulting from a G to C change at position 76 of intron 1;
      ii) a G at position 357 of SEQ ID No: 31 resulting from an A to G change at position 11 of intron 2;
      iii) the sequence ATGTATGT, wherein the first position of the sequence is at position 366 of SEQ ID NO: 31, resulting from a repeat of the ATGT sequence at positions 20-23 of intron 2; and
      iv) an A at position 1398 of SEQ ID NO: 31 resulting from a G to A change at position 225 of exon 3;
   wherein said subject is a mouse and said nucleoticle content indicates an increased cataract susceptibility.

2. The method of claim 1, wherein the CRYGS gene is detected with a primer or probe.

3. The method of claim 2, wherein the primer or probe detects a difference selected from the group consisting of:
   i) a C at position 424 of SEQ ID NO: 30 resulting from a G to C change at position 76 of intron 1;
   ii) a G at position 357 of SEQ ID NO: 31 resulting from an A to G change at position 11 of intron 2;
   iii) the sequence ATGTATGT, wherein the first position of the sequence is at position 366 of SEQ ID NO: 31, resulting from a repeat of the ATGT sequence at positions 20-23 of intron 2; and
   iv) an A at position 1398 of SEQ ID NO: 31 resulting from a G to A change at position 225 of exon 3.

* * * * *